US008202725B2

(12) United States Patent
Kosnik et al.

(10) Patent No.: US 8,202,725 B2
(45) Date of Patent: Jun. 19, 2012

(54) CELL SODDING METHOD AND APPARATUS

(75) Inventors: Paul E. Kosnik, Honolulu, HI (US); Christopher T. England, Kapolei, HI (US); Robert G. Dennis, Chapel Hill, NC (US); Stuart K. Williams, Tucson, AZ (US)

(73) Assignee: Tissue Genesis Incorporated, Honolulu, HI (US)

( * ) Notice: Subject to any disclaimer, the term of this patent is extended or adjusted under 35 U.S.C. 154(b) by 474 days.

(21) Appl. No.: 11/314,281

(22) Filed: Dec. 22, 2005

(65) Prior Publication Data
US 2006/0258004 A1 Nov. 16, 2006

Related U.S. Application Data

(60) Provisional application No. 60/638,199, filed on Dec. 23, 2004, provisional application No. 60/697,954, filed on Jul. 12, 2005.

(51) Int. Cl.
*C12N 5/00* (2006.01)
(52) U.S. Cl. ............... 435/396; 600/36; 623/1.41
(58) Field of Classification Search .............. None
See application file for complete search history.

(56) References Cited

U.S. PATENT DOCUMENTS

| 4,028,190 A | 6/1977 | McAleer et al. |
| 4,820,626 A | 4/1989 | Williams et al. |
| 5,230,693 A | 7/1993 | Williams et al. |
| 5,628,781 A | 5/1997 | Williams et al. |
| 5,753,267 A | 5/1998 | Badylak et al. |
| 5,792,603 A | 8/1998 | Dunkelman et al. |
| 5,928,945 A | 7/1999 | Seliktar et al. |
| 6,352,555 B1 * | 3/2002 | Dzau et al. ........... 623/1.39 |
| 6,416,995 B1 | 7/2002 | Wolfinbarger |
| 6,479,064 B1 | 11/2002 | Atala |
| 6,734,018 B2 | 5/2004 | Wolfinbarger, Jr. et al. |

FOREIGN PATENT DOCUMENTS

| JP | 2000513964 A | 10/2000 |
| JP | 2005519883 A | 7/2005 |
| WO | 95/01419 A | 1/1995 |
| WO | 9749799 A1 | 12/1997 |
| WO | 03053346 A2 | 7/2003 |

OTHER PUBLICATIONS

Matsuda, T., Artificial Organs, 2004, vol. 28 (1), p. 64-71.*
Walluscheck et al., Eur J Vasc Endovas Surg, 1996, vol. 12, p. 321-330.*
Conklin et al., Medical Engineering & Physics, 2000, vol. 22, p. 441-449.*
Sodian et al., Tissue Engineering, 2002, vol. 8, No. 5, p. 863-870.*
Dumont et al., Artif Organs, 2002, vol. 26, No. 8, p. 710-714.*
Jarrell et al. (J Biomech Eng , 1991, vol. 113, No. 2, Abstract.*
Hoerstrup et al., Circulation, 2002, vol. 106, suppl. I, p. I-143-I-150.*
Phillips et al., Ann Thorac Surg 1998, vol. 66, 1191-1197.*
Monney et al., Catheterization and Cardiovascualr Diagnosis, 1997, vol. 40, p. 315-318.*
Hartman, G., Journal of Cardiothoracic and Vascular Anesthesia, 1998, vol. 12. No. 3, p. 358-360.*
Williams et al., Clin Sci (Lond). , 1988, vol. 74, No. 5, Abstract.*
Ahlswede et al., Aterioscler. Thromb., 1994, vol. 14, p. 25-31.*
International Search Report and Written Opinion, Application No. PCT/US06/27191, dated Apr. 9, 2007.
Canadian Office Action in Canadian Application No. 2,615,208, dated Mar. 12, 2010.
Chinese Office Action in Chinese Application No. 200680032989.8, mailed Dec. 25, 2009.
Chinese Office Action in Chinese Application No. 200680032989.8, mailed Oct. 8, 2010.
Australian Office Action in Australian Application No. 2006268129, dated Apr. 22, 2010.
European Search Report in European Application No. 06787137.6, dated Jan. 23, 2009.
European Search Report in European Application No. 06787137.6, dated Feb. 10, 2009.
Japanese Office Action in Japanese Application No. 2008521605, mailed May 17, 2011.
Stuart K. Williams, et al. "Formation of a Multilayer Cellular Lining on a Polyurethane Vascular Graft Following Endothelial Cell Sodding" Journal of Biomedical Materials Research, vol. 26, pp. 103-117 (1992).
Stuart K. Williams et al. "Origin of Endothelial Cells that Line Expanded Polytetrafluoroethylene Vascular Grafts Sodded with Cells from Microvascularized Fat" J Vasc. Surg. 1994; 19: pp. 594-604.
Per-Ake Nygren et al. "Binding Proteins from Alternative Scaffolds" Journal of Immunological Methods 290 (2004) pp. 3-28.
Cora H. P. Arts et al. "A Novel Method for Isolating Pure Microvascular Endothelial Cells from Subcutaneous Fat Tissue Ideal for Direct Cell Seeding" Laboratory Investigation, Oct. 2001, No. 10, pp. 1461-1465.
Stuart K. Williams et al. "Microvascular Endothelial Cell Sodding of ePTFE Vascular Grafts: Improved Patency and Stability of the Cellular Lining" Journal of Biomedical Materials Research, vol. 28, pp. 203-212, 1994.

(Continued)

*Primary Examiner* — Kade Ariani
(74) *Attorney, Agent, or Firm* — Nixon Peabody LLP

(57) ABSTRACT

Tissue engineering methods and biochamber apparatus are provided for making tissue grafts for implantation into a patient. The methods include applying a sustained low magnitude pressure gradient transmurally across a permeable scaffold material using a media containing cells, preferably microvascular epithelial cells, to be deposited on the scaffold for the production of tissue grafts, preferably vascular grafts, to promote accelerated adhesion and maturation of cells on the scaffold material. Biochambers for preparing tubular tissue grafts are provided which contain connectors for holding a graft substrate, proximal and distal tubing for connection to an optional perfusion system, and structure for switching between transmural flow of a cell suspension across the graft substrate and translumenal flow through the lumen of the graft.

18 Claims, 12 Drawing Sheets

OTHER PUBLICATIONS

Dietmar W. Hutmacher et al. "Scaffold-based Tissue Engineering: Rationale for Computer-Aided Design and Solid Free-Form Fabrication Systems" Trends in Biotechnology, vol. 22 No. 7, Jul. 2004, pp. 354-362.

Valerie Liu Tsang et al. "Three-Dimensional Tissue Fabrication" Advanced Drug Delivery Reviews 56 (2004) pp. 1635-1647.

Maria A. Rupnick, PhD et al. "Endothelialization of Vascular Prosthetic Surfaces After Seeding or Sodding with Human Microvascular Endothelial Cells" J Vasc. Surg. 1989; 9; pp. 788-795.

Chinese Office Action in Chinese Application No. 200680032989.8, mailed Dec. 7, 2011.

* cited by examiner

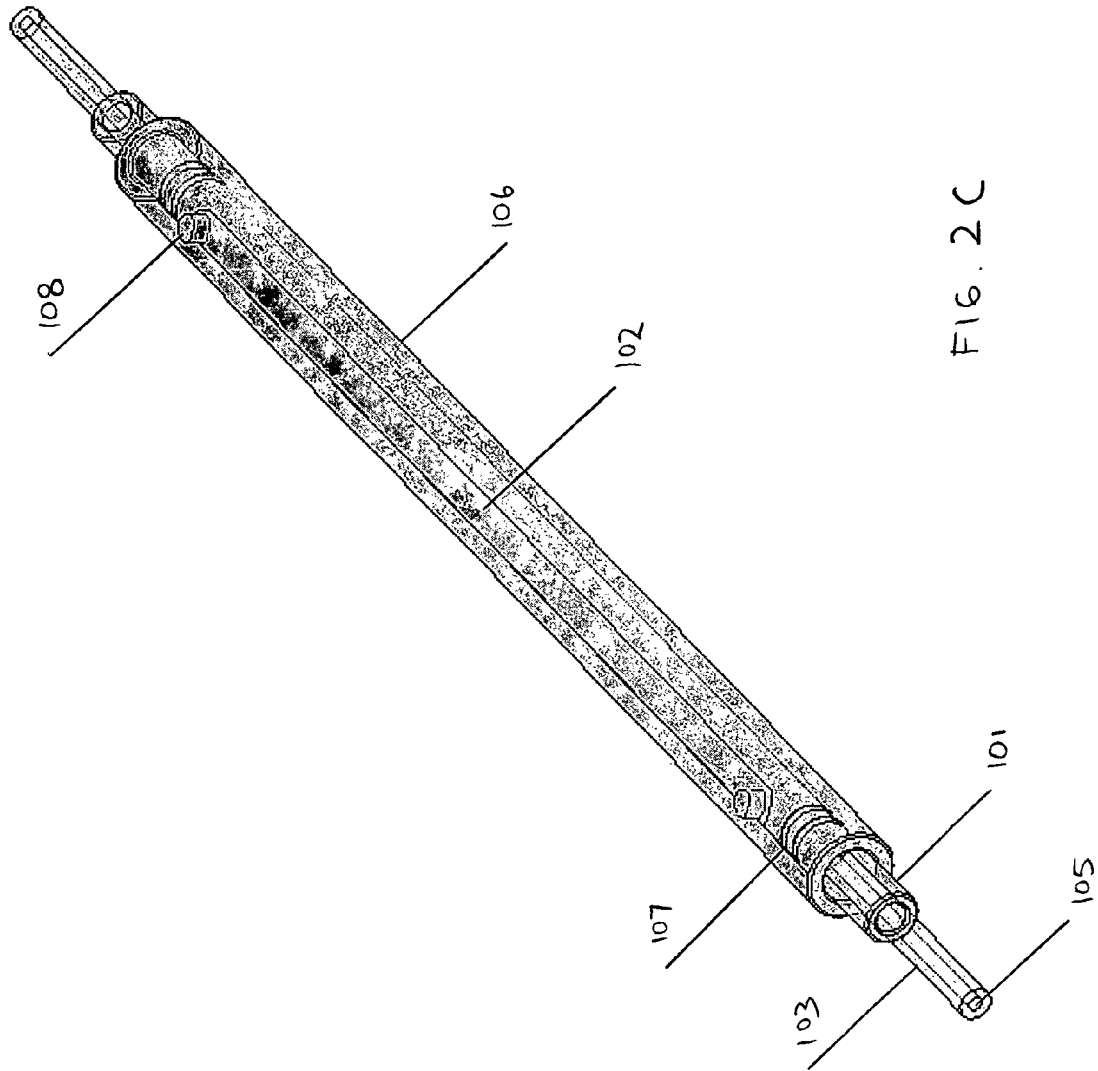

CELL SODDING METHOD AND APPARATUS

This application claims priority to U.S. patent application Ser. No. 60/638,199, filed on Dec. 23, 2004, which is hereby incorporated by reference herein, and further claims priority to No. 60/697,954, filed on Jul. 12, 2005.

STATEMENT REGARDING FEDERALLY SPONSORED RESEARCH OR DEVELOPMENT

This invention was made with Government support under #W81XWH-04-1-0503 and #W81XWH-05-1-0620 awarded by the United States Army Medical Research and Materiel Command.

FIELD OF THE INVENTION

The present invention relates to tissue engineering systems for the manufacture of tissue implants and grafts, including, but not limited to, prosthetic vascular and arteriovenous grafts. The present invention relates, in particular, to methods and apparatus for adhering cells to permeable scaffold materials by sustained low pressure cell sodding, which includes applying a sustained pressure gradient across a permeable material using media containing cells to be deposited on the material. The methods and the apparatus of the invention promote accelerated adhesion and maturation of cells.

BACKGROUND OF THE INVENTION

Tissue engineering is developing toward clinical applications for the repair and restoration of damaged or diseased tissues and organs. In particular, the development of vascular grafts is a major goal in the field of vascular surgery. Cardiovascular disease is the leading cause of mortality and morbidity in the first world. The standard of care, the autograft, is not without serious morbidity. Patients with systemic disease, leaving no appropriate autograft material or having already undergone autografts, number 100,000 a year in the United States alone and have few autograft options.

Vessels have mechanical and biological failure modes caused by thrombosis within the vessel and subsequent occlusion and/or cellular ingrowth. Synthetic vessels having material properties capable of withstanding arterial pressure are commonplace, making the search for non-thrombogenic materials a prime research interest. Endothelial cells obtained from the patient have been shown to decrease the thrombogenicity of implanted vessels (Williams et al., 1994, *J. Vasc. Surg.,* 19:594-604; Arts et al., 2001 *Lab Invest* 81:1461-1465), but to date placement of the cells upon the graft have been lengthy processes not suited to the operating room.

Pressure gradients involving transient (from a few seconds to less than one minute) relatively high pressures (5 PSI or 259 mm Hg) have previously been used to deposit cells onto a porous graft scaffold. The cells are deposited by a sieving action provided by bulk flow of a cellular suspension against a substrate or scaffold material having pores smaller than the cell population, thus capturing cells in the matrix (e.g., U.S. Pat. No. 5,628,781; Williams et al., 1994, *J. Vasc. Surg.,* 1Q: 594-004; Williams et al., 1992, *J Biomed Mat Res* 26:103-117; Williams et al., 1992, *J. Biomed Mat Res* 28:203-212). The captured cells have been shown to subsequently adhere to the scaffold material to improve the patency of peripheral grafts. However, clinical applicability in the coronary position has been limited to date, at least in part because the resulting vessels do not maintain sufficiently cohesive non-thrombogenic surfaces. In response, research has focused on additional cell maturation time in vitro.

What is needed are methods and apparatus to achieve rapid cellular adhesion in or on permeable substrate materials in a matter of minutes or hours, with instruments that lend themselves to the operating room environment, maintain a sterile barrier, are easy to use, produce consistent graft results and are relatively inexpensive.

BRIEF SUMMARY OF THE INVENTION

The present invention is based, in part, on the inventors' surprising discovery that a sustained low pressure gradient across a graft scaffold or substrate material for about 1 minute up to about 24 hours, preferably in a cell perfusion system, provides significantly more rapid and uniform cell adhesion and maturation on substrate materials than the transient high-pressure gradients employed by known methods. Furthermore, application of a sustained low pressure gradient reduces stress, damage to the cells, and unnecessary activation of the cells during the adhesion process. Employing sustained low magnitude pressure also provides greater control over cellular activation and differentiation pathways by inducing less shear stress, a lack of control of which have impeded previous tissue engineering efforts.

In one embodiment the present invention provides a method of preparing a tissue graft for implantation into a patient, including the steps of providing a biochamber containing a porous substrate, introducing a suspension of cells into the biochamber, and applying a low pressure transmural flow of the suspension of cells across the substrate for a duration sufficient to adhere the cells to the substrate, wherein the pressure is about 10 to about 60 mmHg for a duration of at least 5 minutes.

In another embodiment the invention provides a method of implanting a vascular tissue graft. In this method, microvascular endothelial cells ("MVECs") are harvested from a patient in need of a vascular graft. A biochamber containing a tubular graft scaffold is provided and media containing the microvascular endothelial cells is introduced into the biochamber. A sustained low pressure transmural flow of about 10 to about 60 mmHg of the media is then applied across the scaffold to provide an endothelialized vascular tissue graft. The graft is then implanted into the patient.

The present invention also provides cell sodding biochambers for the manufacture of vascular grafts, which biochambers provide for controlled sustained transmural flow, optionally followed by translumenal flow, thereby providing sustained pressure gradients across a porous material for preparing vascular tissue implants and grafts via adherence, growth, and differentiation of the cells.

One embodiment of a biochamber for preparing a tissue graft includes an outer sleeve having a proximal end and a distal end, an inner sleeve at least partially disposed within the outer sleeve and having proximal and distal ends and a trough between these ends. The trough is disposed within the outer sleeve to define an interior space between the inner and outer sleeves. The biochamber further includes a distal interior conduit extending from within the distal end of the inner sleeve, and a proximal interior conduit extending from within the proximal end of the inner sleeve. Intracapillary posts are provided within the interior space, and adapted to hold a tubular graft scaffold between the distal interior conduit and the proximal interior conduit. The graft scaffold defines an intracapillary and an extracapillary space. The outer sleeve further includes at least one extra-lumenal port for providing transmural flow through the graft.

In a particularly preferred embodiment a biochamber in accordance with the present invention is connected to an automated perfusion system such as those disclosed in U.S. patent application Ser. Nos. 09/967,995 and 10/109,912, which are incorporated by reference herein in their entirety.

Additional advantages and features of the invention will become more readily apparent from the following detailed description and drawings which illustrate various embodiments of the invention.

BRIEF DESCRIPTION OF THE DRAWINGS

FIGS. 2A-2D show views of another biochamber in accordance with the present invention. This embodiment employs a tubular configuration. Ancillary equipment, such as a stopcock for introduction of cells, Y-connector for application of transmural and translumenal flow, and associated automated perfusion equipment are not shown. Such equipment may be any suitable equipment, including, but not limited to, as shown in FIG. 1 and FIG. 3.

DETAILED DESCRIPTION OF THE INVENTION

Figure 1:
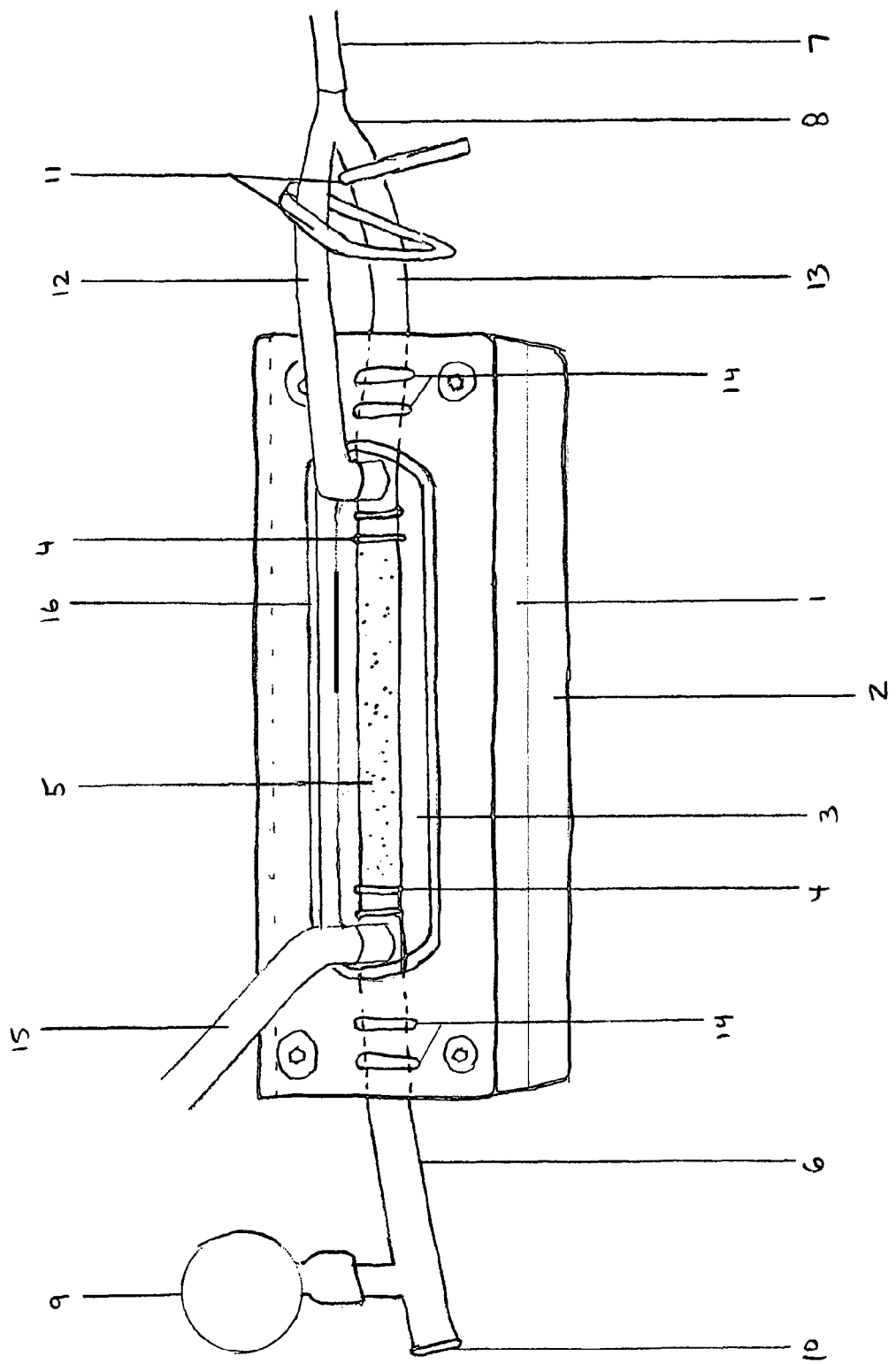
FIG. 1 shows a vessel biochamber in accordance with the present invention and having a proximal stopcock for the introduction of cells, and a Y-connector allowing for the application of transmural pressure, followed by luminal flow.
Figure 2A:
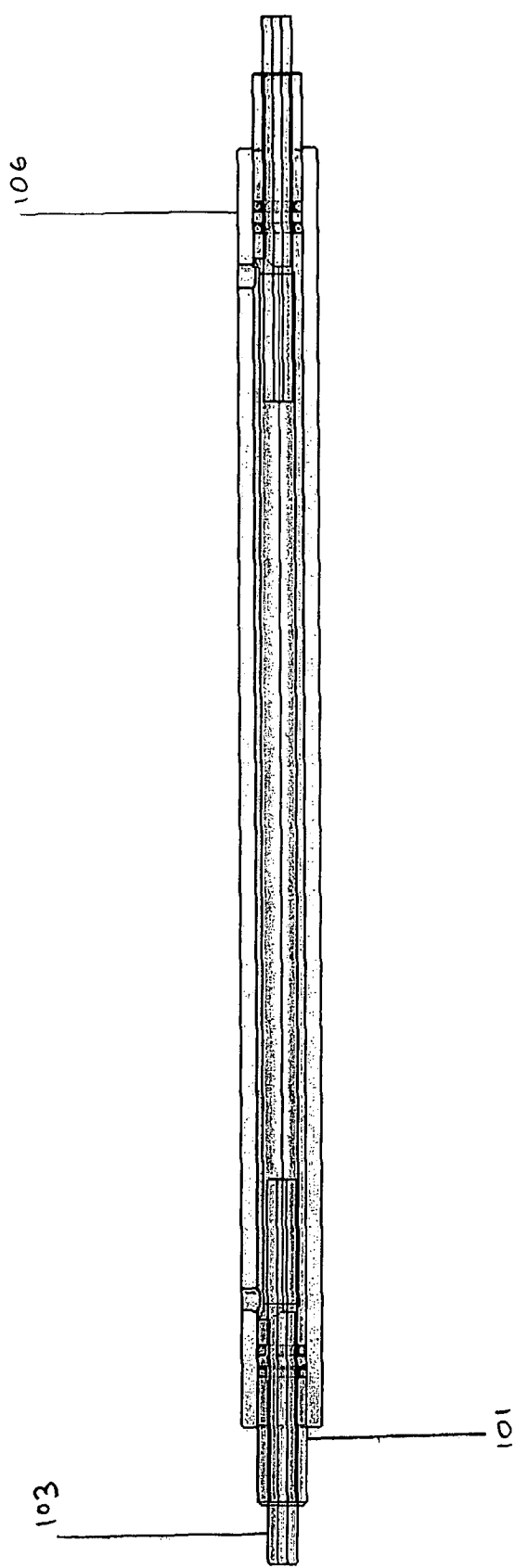
Figure 2B:
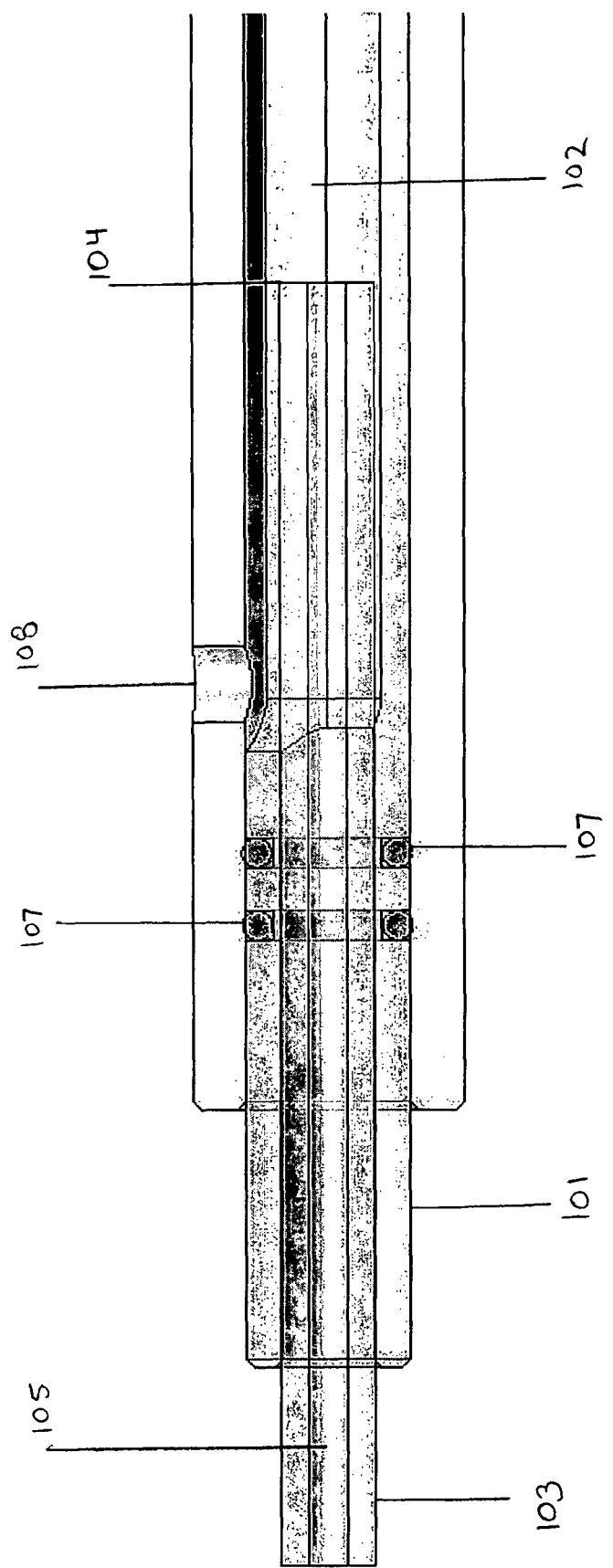
Figure 2D:
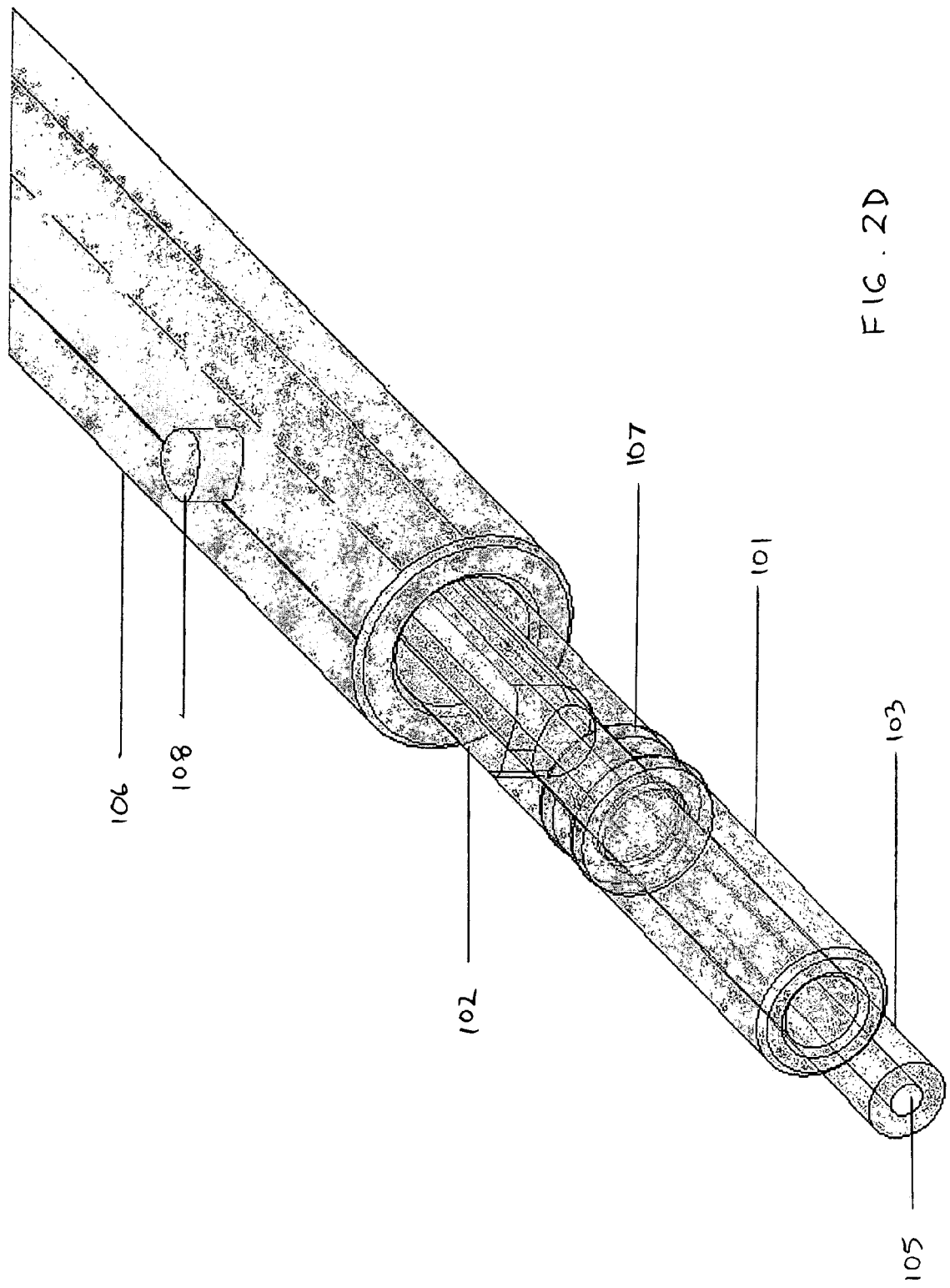

The present invention provides methods for preparing tissue implants and grafts by applying sustained low magnitude pressure to sod cells onto a porous substrate material. Furthermore, the present invention provides preferred cell sodding biochambers which comprise two separate flow-through spaces, and mechanisms and structure to provide controlled, sustained differential pressure gradients across permeable scaffold or graft substrate materials.

The apparatus and methods of the present invention are useful for preparing various tissue implants or grafts by applying sustained low magnitude pressure for adhering or "sodding" cells onto any suitable graft scaffolds or other porous substrate materials. In a specific embodiment, the tissue is a tubular tissue, such as a vascular tissue. However, the invention also is applicable to making other types of tissue grafts involving the adhesion of cells to permeable scaffolds or other permeable substrate materials of any shape or size. The resulting tissue grafts include, but are not limited to, skin, cartilage, bone, bone marrow, tendon, ligament, gastrointestinal tract, genitourinary tract, liver, pancreas, kidney, adrenal gland, mucosal epithelium, and nerve grafts.

The term "low magnitude pressure" as used herein means pressure having a head of about 10 mmHg to about 60 mmHg, more preferably about 20 to about 55 mmHg and most preferably about 35 to about 50 mmHg. The pressure is preferably sustained, i.e., continuously applied, for about 1 min, about 10 min, about 20 min, about 30 min, about 40 min, about 50 min, about 1 hour, about 1.5 hours, about 2 hours, about 2.5 hours, about 3 hours, about 4 hours, about 5 hours or about 6 hours, to enhance the adhesion, growth and differentiation of the cells. One of ordinary skill in the art can select appropriate low magnitude sustained pressures gradients and durations according to the types of cells, tissue grafts and substrate materials, given the teachings herein. For human MVEC sodding, for example, pressures of about 50 mmHg for a sustained duration of about 5 minutes are particularly preferred.

The cells to be adhered may include, for example, fibroblasts, smooth muscle cells, pericytes, macrophages, monocytes, plasma cells, mast cells, adipocytes, tissue-specific parenchymal cells, endothelial cells, urothelial cells, and various other cell types encountered in tissue engineering applications, including undifferentiated adult stem cells from various tissue sources. In a preferred embodiment, the adherent cells are endothelial cells, more preferably human microvascular endothelial cells ("MVEC") obtained from microvascular rich tissue according to the methods disclosed in U.S. Pat. Nos. 4,820,626 and 5,230,693. The adherent cells may be autologous, allogeneic, or xenogeneic, but preferably are autologous in origin.

In a particularly preferred embodiment the adherent cells are MVECs derived from human adipose tissue, and contain at least a fraction of adipose-derived stem cells. The stem cell fraction may be the same as that fraction found in adipose tissue or may be further purified to produce a cellular suspension of MVECs having a high concentration of stem cells per total number of cells in the suspension. We have found that excellent results can be obtained without isolating or concentrating the adipose-derived stem cell fraction. In a particularly preferred embodiment, the graft is sodded with a MVEC suspension derived from adipose tissue of a human patient that is the same patient intended to receive the resulting MVEC sodded graft or implant.

The sodding can be carried out by injecting cells to be sodded into an aqueous perfusion media or by first creating a cellular suspension of the desired cells and employing this suspension as the perfusion media. In either case, a sustained low magnitude pressure will be applied to drive the suspended cells against a permeable substrate, for example, a tubular graft scaffold for a vascular tissue graft. The cellular slurry or suspension may be obtained by any suitable method, including culturing a quantity of cells and dispersing the cultured cells in media. In a preferred embodiment, the suspension or slurry is prepared by harvesting adipose tissue via, for example, a liposuction technique, then mincing the tissue and subjecting the minced tissue to various enzymes, centrifugation, and resuspension to prepare an adipose-derived MVEC suspension. These and similar techniques can be applied to non-adipose tissue to prepare other types of cell suspensions or slurries for use in the sodding method of the present invention.

Prior to sodding the graft substrate may be pretreated with a protein, preferably albumin. The substrate also may be a preclotted or pretreated with a plasma. In certain embodiments such pretreatments can serve to further enhance the adherence, spreading, and growth of tissue cells on the substrate material.

The graft substrate (or "scaffold") materials used in the present invention may be any permeable material of various sizes and geometries. The material may be synthetic, including, but not limited to, expanded poly-tetra fluoro ethylene (ePTFE), polyurethane, polypropylene, polyethylene, polyamides, nylon, elastin, polyethylene terephthalate, polycarbonate, and silicone. In other embodiments, the graft scaffold may be a biopolymer, such as elastin or collagen. The graft substrates or scaffolds may be constructed by any suitable method, including, but not limited to, those referred to in Liu, T. V. et al., 2004, Adv. Drug. Deliv. Rev. 56(11):1635-47; ; Nygren, P. A. et al., 2004, J. Immunol. Methods 290(1-2):3-28; Hutmacher, D. W. et al., 2004, Trends Biotechnol. 22(7): 354-62; Webb, A. R. et al., 2004, Expert Opin. Biol. Ther. 4(6):801-12; ; and Yang, C. et al., 2004, BioDrugs 18(2):103-19.

The graft substrate is then mounted in an apparatus capable of providing sustained low magnitude pressure to provide transmural flow of the cellular suspension in relation to the substrate. Preferred apparatus for vascular grafts are disclosed below, but any suitable apparatus may be used, provided it can hold the substrate in place while containing and subjecting the substrate to sustained transmural pressure gradients of between about 10 to 60 mmHg. In an especially preferred embodiment, the apparatus is a biochamber further including mechanisms to provide translumenal flow, after deposition of the cells by transmural flow.

The term "transmural pressure or flow" as used herein means pressure or flow from one side to the other side of a graft scaffold, across the wall of the graft scaffold. Where the graft scaffold is a tubular graft scaffold, the transmural pressure flow is preferably from the lumen or intracapillary ("IC") space of the graft to the outside or extracapillary ("EC") space of the graft.

The term "translumenal pressure or flow" as used herein refers to pressure or flow longitudinally through the lumen of a tubular graft. The terms "translumenal flow" and "translumenal perfusion" may be used interchangeably. Translumenal perfusion may be applied, for example, after transmural flow, to provide a training or cleansing effect on the deposited cells. In this case, translumenal flow rates up to and including physiologic flow rates (up to about 160 ml/min) are preferred. Transmural flow rates as low as about 5 ml/min according to the methods herein are sufficient to provide cellular adhesion capable of withstanding subsequent supraphysiologic flow.

The term "proximal" as used herein refers to a point of reference on the side of media inflow in relation to the center of a biochamber.

The term "distal" as used herein refers to a point of reference on the side of media outflow in relation to the center of the biochamber.

The term "intracapillary (IC)" refers to the lumen or the internal space of a tubular graft scaffold and may be interchangeably referred to as "intralumenal."

The term "extracapillary (EC)" refers to the outside space of a tubular graft scaffold and may be interchangeably referred to as "extravascular" or "extralumenal."

While the methods of the invention may be carried out in any suitable apparatus, we have found that particular biochamber designs and automated perfusion systems are especially well-suited to achieve optimal results in terms of consistent and uniform cell adherence and operator convenience.

A vessel biochamber in accordance with one embodiment of the present invention is shown in FIG. 1. The biochamber includes two halves comprising a top vessel 1 and a bottom vessel 2, each having a proximal end and a distal end. The vessels are mutually disposed to define an interior space 3 by virtue of a double O-ring seal 16. Intracapillary (IC) double barb connectors 4 are positioned within the space defined by the vessels. The connectors 4 are adapted to hold a graft scaffold 5 at each of the proximal and distal ends of the biochamber. A proximal tubing 6 connects to the IC connector to provide an IC flow in relation to the graft scaffold 5. Distal tubing 7 connects the distal IC and distal EC flow spaces via a Y-connector 8. The IC tubing 6 and 13 are sealed upon entry to the biochamber by virtue of a pair of O-rings 14 on each side. The biochamber may include an additional extravascular port 15.

The permeable scaffold material may be mounted via the connectors 4 to the IC proximal 6 and distal tubing 13. In a specific embodiment, the biochamber includes a stopcock 9 attached to the proximal tubing 6 via a T-connector 10, to allow for injection of cells into the biochamber. In yet another specific embodiment, the biochamber further includes at least one clamp or valve 11 that can close either the distal EC tubing 12 or the distal IC tubing 13 to create, or shift between, transmural or translumenal pressure gradients, as explained below. In a preferred embodiment, each of the distal IC tubing 13 and the distal EC tubing 12 has its own valve or slide clamp.

Preferably, the top and the bottom vessels of the biochamber are made of optically clear materials (e.g., polystyrene or polycarbonate) so that intra- and extra-luminal flow can be visually monitored. The biochamber is preferably made from materials which are autoclavable, gamma, or gas-sterilizable. Furthermore, the biochamber may contain a multiple silicone O-ring system, providing double seal contact for vessel attachment so that the vessel length and angular position may be adjusted after a specimen is mounted between the two barbs within the biochamber. In addition, metal thread inserts may be used to eliminate the need for threading manufactured components, and also eliminate the potential failure of plastic threads.

The configuration of the distal tubing 7, 12, 13, which couples the distal IC and distal EC flow spaces, allows the operator to switch between a transmural pressure gradient and a translumenal pressure gradient using the slide clamps 11, or in automated fashion within a bioreactor. This switch would typically take place to provide translumenal pressure after cell adhesion. In a specific embodiment, cells are introduced via stopcock 9 or a septum connected via a T-connector 10 to the proximal tubing 6. The distal IC slide clamp 11 is then closed to allow only outflow from the EC space, thereby establishing a transmural pressure gradient from the proximal IC to distal EC space, and a small flux of media through the permeable scaffold while depositing adhering cells on the lumenal surface and/or within the wall of the graft. The pressure gradient may be established either by generation of a positive pressure at the proximal IC side, a negative pressure at the distal EC side, or a combination of positive pressure at the proximal IC and negative pressure at the distal EC spaces. If desired, after cell adhesion to the lumenal surface, the distal EC slide clamp may be closed and the distal IC slide clamp opened to allow flow through the lumen of the vessel to ensure cellular adhesion in the presence of a shear stress, which simulates a physiological environment.

The controlled, sustained differential pressure gradient across the permeable scaffold material may be created by any suitable configuration, including, but not limited to, gear pumps, peristaltic pumps, diaphragm pumps, centrifugal pumps, and passive pressure heads created by a column of fluid, so long as the pressure is sufficiently sustained and at a magnitude sufficient to achieve the advantages of the invention. In a particularly preferred embodiment, the pressure is applied transmurally to a vascular graft scaffold using media containing endothelial cells at a pressure head of about 50 mmHg and for a duration of about 5 minutes.

Another embodiment of a preferred apparatus for cell sodding is the tubular biochamber shown in FIGS. 2A-2D. A barb-to-barb connector (not shown) is fitted into the interior ends of two pieces of tubing 103, preferably hard silicon tubing, that rests in a "trough" 102 of an inner sleeve 101. A vascular graft is attached to both barbs, thereby defining the interior intra-vascular flow (IVF) space or lumenal flow space. This space lies within the trough 102 created by the inner sleeve 101 and is sealed from the exterior by virtue of an interference fit between the hard silicone tubing 103 and the inner sleeve ID. IVF flow can then be initiated by connecting the two pieces of silicone tubing 103 to any flow system through the intra-lumenal ports 105. The biochamber is then sealed by sliding the inner sleeve 103 into the outer sleeve such that both pairs of O-rings 107 are within the outer sleeve. Extra-vascular flow (EVF) is accomplished by a pair of threaded barbs (not shown) attached to the extra-lumenal ports 108. The EVF is sealed from the exterior by virtue of the double O-ring 107 at each end of the inner sleeve. Transmural flow is accomplished by flowing into the lumenal space proximally by way of the silicone tubing and clamping the lumenal space distally while opening the EVF to the pump return via tubing connections to either or both of the extra-lumenal ports 108. Not shown are threaded barb connectors on the outer sleeve at the extra-lumenal port, and barbs and a graft attached to the two hard silicone tubes in the interior trough of the inner sleeve.

The preferred biochambers of the present invention have: 1) two independent flow spaces for lumenal and extravascular flow, 2) silicone O-ring clamps to provide double seal contact, 3) minimal number of threaded fasteners, minimizing handling time and production cost, 4) optically clear materials for visualization of specimen and intra- and extra-lumenal flows, 5) manufacturable from autoclavable and gas sterilizable materials, 6) embedded multiple silicone O-ring system for vessel attachment to allow vessel length and angular position to be adjusted after specimen mounting, and 7) metal thread inserts to eliminate the need for threading manufactured components, and eliminate failure of plastic threads. In addition, an automated rocking bed or other rotating apparatus may be provided to facilitate even distribution of the cells within the lumen of the vessel during pressure sodding. The rocking bed may fit within and be powered by an automated perfusion system, and the biochamber may fit within the rocking bed. However, a rocking bed is not required for complete 360 degree coverage of the graft.

The tubular configuration of FIG. 2 has all of the benefits listed above, and in addition includes the following benefits: tool-less open/close, minimal volume, convenient length and rotational adjustment of graft, lengthwise scale-up, and pressures balanced such that leakage does not occur by virtue of the O-ring sealing mechanism.

The methods and biochamber apparatus of the present invention may be employed in combination with various media perfusion systems. The advantages of the invention may be optimized for certain tissue engineering applications by use of an automated cell culture apparatus, preferably as described in U.S. patent application Ser. Nos. 09/967,995 and 10/109,712.

The above-referenced patent applications provide automated perfusion culture platforms to provide controlled media flow, shear stress, nutrient delivery, waste removal, and improved mass transfer. These address many of the shortcomings of traditional culture systems by providing a sterile barrier to contamination while maintaining more uniform and controlled physiologic environments for cells and tissues, providing the user with sample access and data, and providing affordable reproducibility and reliability with data tracking and logging.

Figure 3:
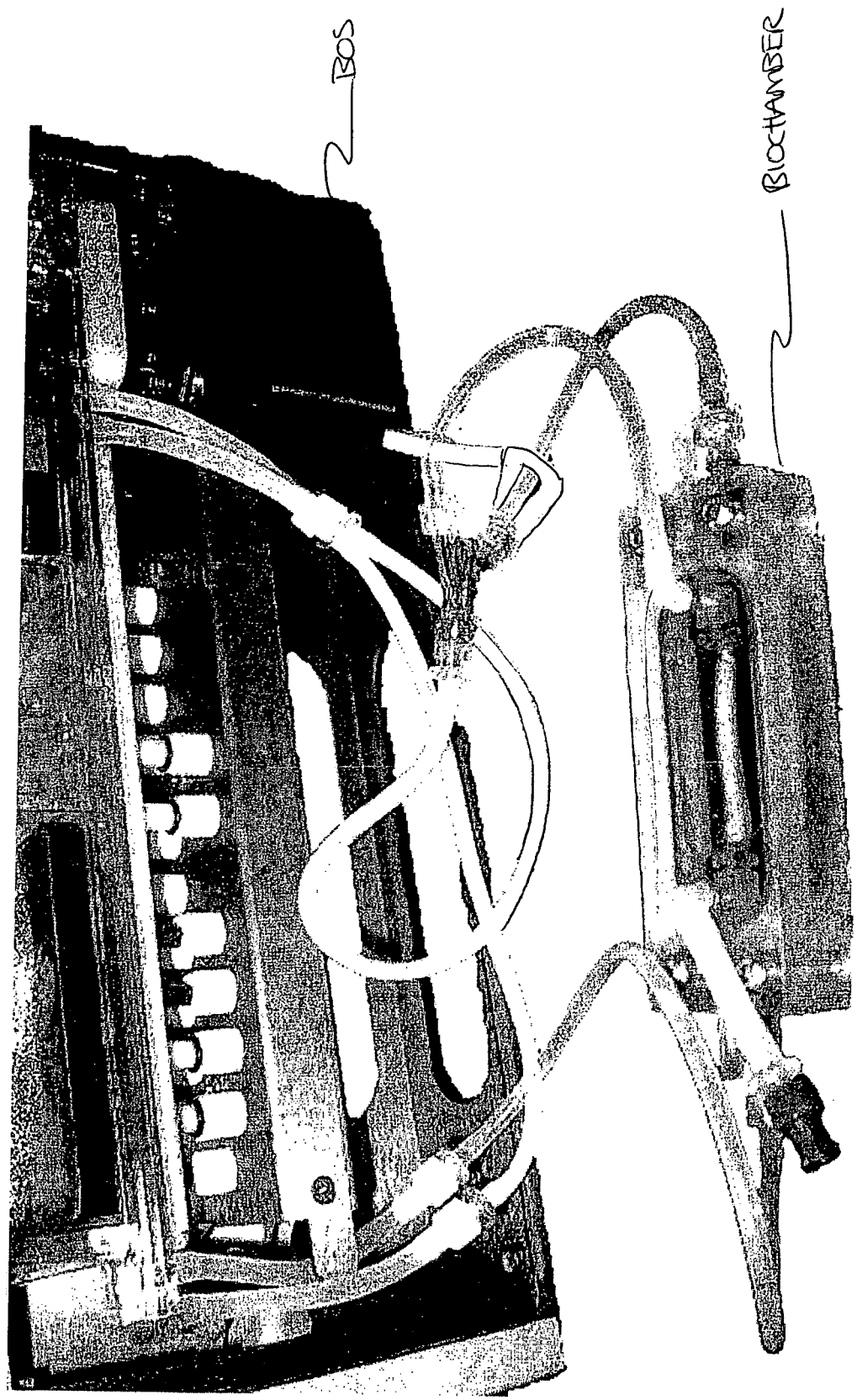
FIG. 3 shows a Bio-Optimization System, "BOS" (TM), Tissue Genesis, Inc. (Honolulu, Hi.), automated cell perfusion system, as disclosed in U.S. patent application Ser. Nos. 09/967,995 and 10/109,912, connected to a vessel biochamber as shown in FIG. 1 and fitted with an elastin vascular graft conduit.

Such an automated perfusion system (FIG. 3) may include a durable cartridge containing a pump, valve array, flow meter, and user interface. It preferably has an embedded microcontroller and pre-programmed flow regimes with programmable flow states. Multiple perfusion loop cartridges may be housed within a single docking station rack, designed to be housed within a laboratory incubator. The disposable perfusion flowpath integrates with the cartridge and may have integrated media reservoirs, tubing for gas exchange, and a valve matrix controlling media flow. A biochamber in accordance with the present invention may be mated with the flowpath. Periodic flow reversal can be employed to decrease differences in media composition from inlet to outlet. An automated sampling system also may be provided to allow the user to obtain a sample of media for analysis. Flow rates may vary from, for example, 1 up to 120 ml/min or more; flow may be monitored by an optical drop meter.

Because the preferred flow for the current invention is transmural, the flow rate is dependent upon the permeability of the graft material, and decreases as the cells are applied to the lumenal surface. Transmural flow rates before the introduction of cells can be from 5-50 ml/min depending on the graft material and generally decrease to 1-10 ml/min after the introduction of cells. Preferred endothelial cell numbers include 120,000-2,000,000 cells/cm$^2$ of luminal surface area, more preferably about 250,000 cells/cm$^2$.

The following examples illustrate the methods and apparatus of the present invention. These examples should not be construed as limiting.

EXAMPLE 1

We used a sustained low pressure head (10-50 mmHg) to maintain a transmural pressure gradient for 1 min up to 24 hours to seed early passage microvascular endothelial cells isolated from adipose tissue onto commercially obtained (Impra) expanded Teflon (ePTFE) small diameter grafts (3-4 mm Inner Diameter). The microvascular endothelial cells were obtained according to the method of U.S. Pat. Nos. 4,820,626; 5,230,693; and 5,628,781. Grafts were primed with 70% ethanol which was then replaced with media (M199, Invitrogen) containing 20% FBS (Invitrogen) and antibiotics (Invitrogen) prior to being mounted in vascular biochambers. The cells were introduced into the biochamber at a density of $1 \times 10^6$ cells/cm$^2$.

Figure 4:
FIG. 4 is a 400× fluorescent image of endothelial cells on an ePTFE graft surface, immunostained to demonstrate von Willebrand Factor and nuclei. Approximately $2\times10^6$ cells were pressure sodded onto the graft with a pressure head of about 20 to 28 mmHg for 6 hours, with manual rotation 180°, then 90°, then 180° of the biochamber every hour during sustained low magnitude pressure sodding. After 6 hours, the graft was translumenally perfused with culture medium at about 5 to 8 mL/min for 18 hours.
Figure 5:
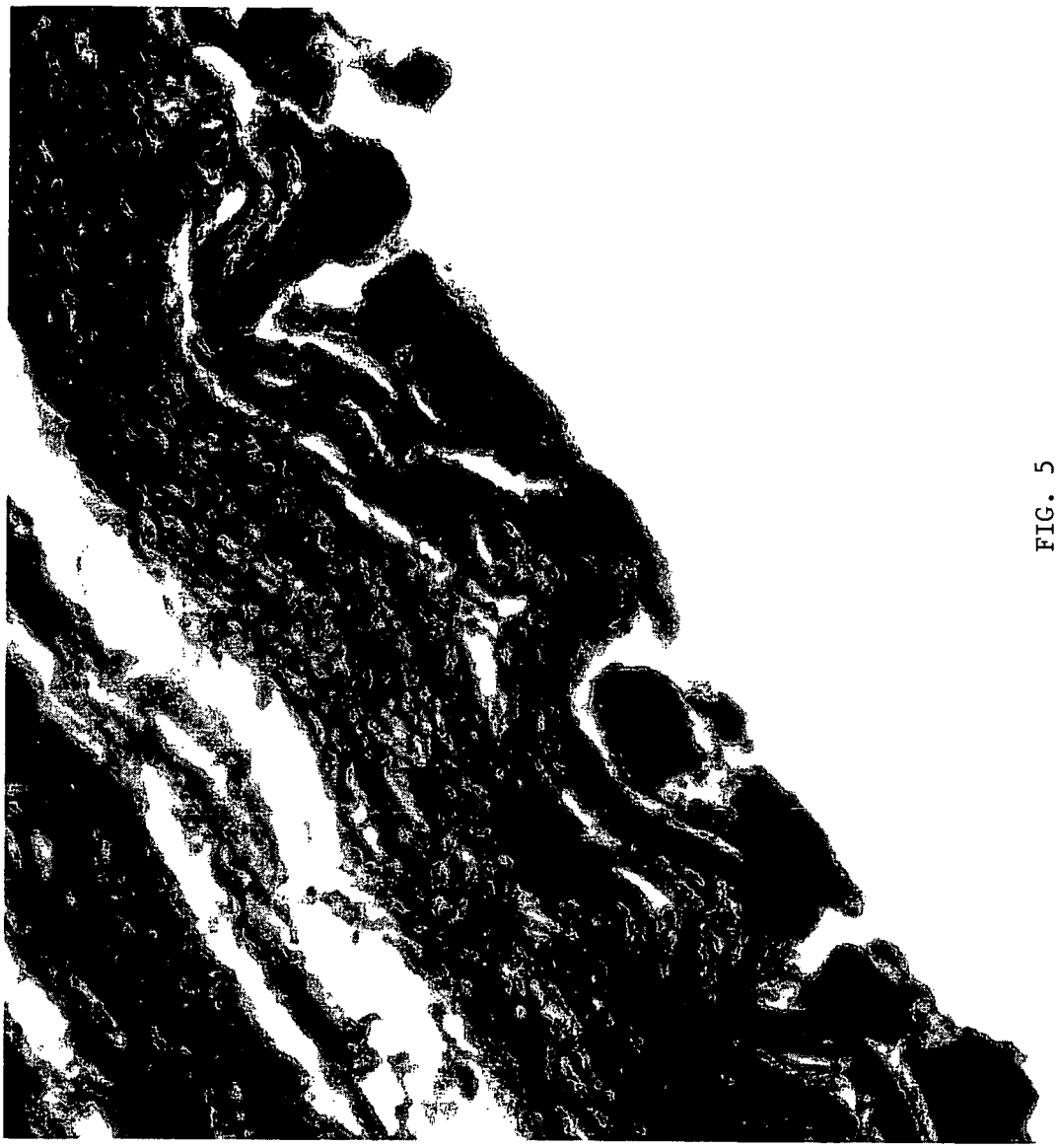
FIG. 5 shows porcine derived microvascular endothelial cells pressure sodded onto an elastin graft for 6 hours. The graft was removed and fixed in 10% neutral buffered formalin (90% DPBS), dehydrated, cleared, infiltrated with and imbedded in paraffin, and sectioned at 6 micrometers before being stained with Hematoxylin and Eosin.

In a series of experiments with transmural pressure, followed, in some cases, by lumenal perfusion, endothelial cells were shown to actively adhere to the ePTFE and elastin surfaces. A microscopic view of cross sections after 6 hours of perfusion showed expression of von Willebrand Factor, cell-cell interactions and cells spreading on both ePTFE (FIG. 4) and elastin surfaces (FIG. 5).

The method resulted in rapid cell adhesion, spreading, and subsequent formation of a cohesive cell layer expressing von Willebrand Factor, a morphologic marker for endothelium, and the requisites for clinical application of the grafts. (See, e.g., Rupnick et al., 1989, *J. Vasc Surg* 9:788-795). While not wishing to be bound by theory, we believe that low magnitude sustained pressure allows for more rapid cellular adhesion, spreading, and development of cell-cell interactions by stimulating cellular maturation of the cells, particularly of endothelial cells, which are sensitive to flow and shear stresses. The practical result is a new ability to rapidly create grafts, including but not limited to, vascular grafts with endothelial linings. The advantages of this method include: 1) smaller pressure heads (as little as 10 mmHg differential pressure is sufficient, as compared with 250 mmHg used for typical transient pressure applications); 2) endothelial cell adhesion and maturation are increased, as compared with acute application of pressure; and 3) the vessels can be readily switched from transmural pressure (pressure sodding mode) to lumenal flow (perfusion mode) without removal of the graft from the bioreactor.

EXAMPLE 2

Figure 6:
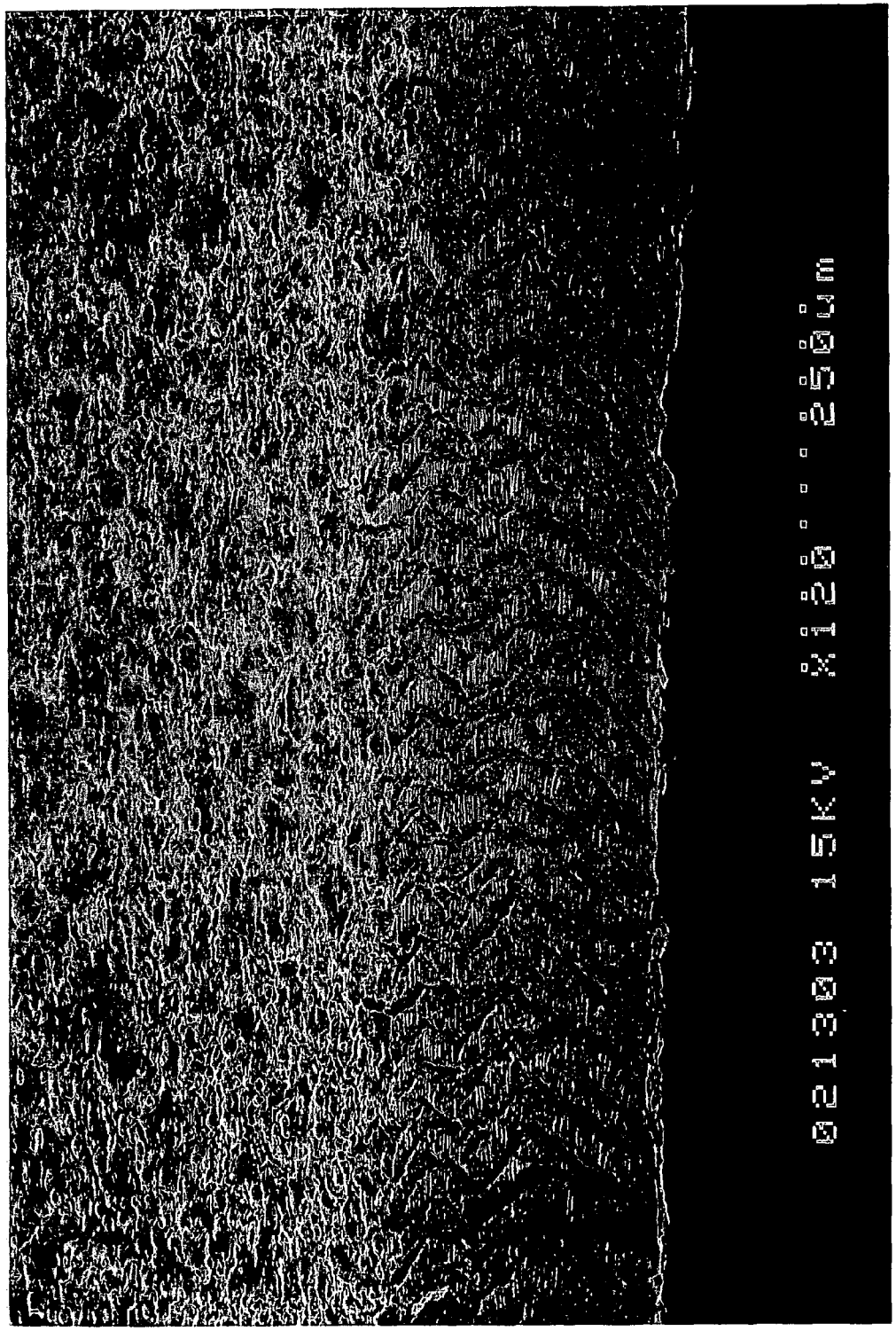
FIG. 6 is a scanning electron micrograph (×120 magnification) showing adherent endothelial cells (top layer) on an expanded Teflon (ePTFE) conduit (bottom layer) sodded with $0.82\times10^6$ MVEC cells/cm$^2$ for 4 hours (about 20 mmHg) using the biochamber of FIG. 1.

An ePTFE graft was cleared using 10 min 70% EtOH, then 10 min 100% EtOH, then 24 hours in MVEC media (M199E, 1 µg/mL Amphotericin B, 20 µg/mL Penicillin/Streptomycin, 15% heat-inactivated FBS). The graft was then sodded with $0.82 \times 10^6$ MVEC cells/cm$^2$ with a BOS gear-pump pressure head of about 20 mmHg for 4 hours. The sodded graft was then fixed in 10% neutral-buffered formalin and embedded in paraffin, then sectioned. After histoanalysis, one of two blocks was melted down, the ePTFE deparaffinized, and dehydrated in 100% EtOH. The resulting sodded graft was then critical point dried, mounted, and sputter coated for SEM, and imaged on an Hitachi S-800 field-emission SEM. FIG. 6 shows an SEM image of endothelial cell adhesion on an ePTFE graft substrate sodded with $0.82 \times 10^6$ MVEC cells/cm$^2$ for 4 hours (about 20 mmHg).

EXAMPLE 3

Figure 7:
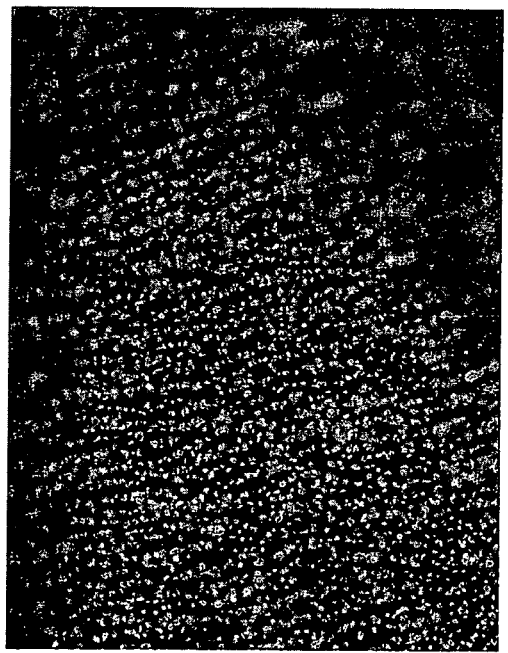
FIG. 7 shows the proximal and distal ends of a 10 cm long vascular ePTFE graft sodded using the biochamber of FIG. 2 with $5\times10^5$ cells/cm$^2$ for 10 minutes (about 50 mmHg) transmurally, followed by 20 minutes of luminal flow (10 mL/min), resulting in highly uniform cell adhesion at each end of the long graft.
Figure 7:
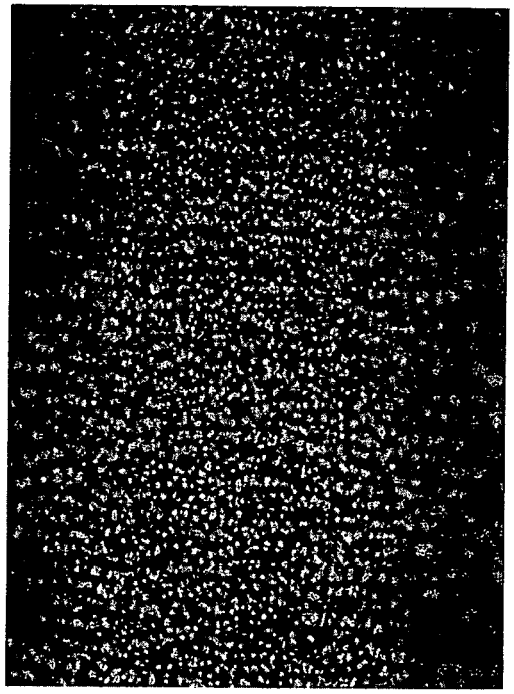

We denucleated a 4 mm internal diameter ePTFE graft substrate having a length of 10 cm using 10 min 70% ethanol, then 10 min 100% ethanol. The graft was then sodded in a biochamber as shown in FIG. 2 at $5 \times 10^5$ cells/cm$^2$ by applying 10 minutes transmural flow (~50 mmHg), followed by 20 minutes luminal flow (10 mL/min). The resulting MVEC-sodded graft was fixed, stained with BBI, and imaged. FIG. 7 shows the proximal and distal ends of a 10 cm long vascular ePTFE graft sodded with $5 \times 10^5$ cells/cm$^2$ for 10 minutes (about 50 mmHg) transmurally, followed by 20 minutes of luminal flow (10 mL/min), resulting in highly uniform cell adhesion at each end of the long graft.

Figure 8:
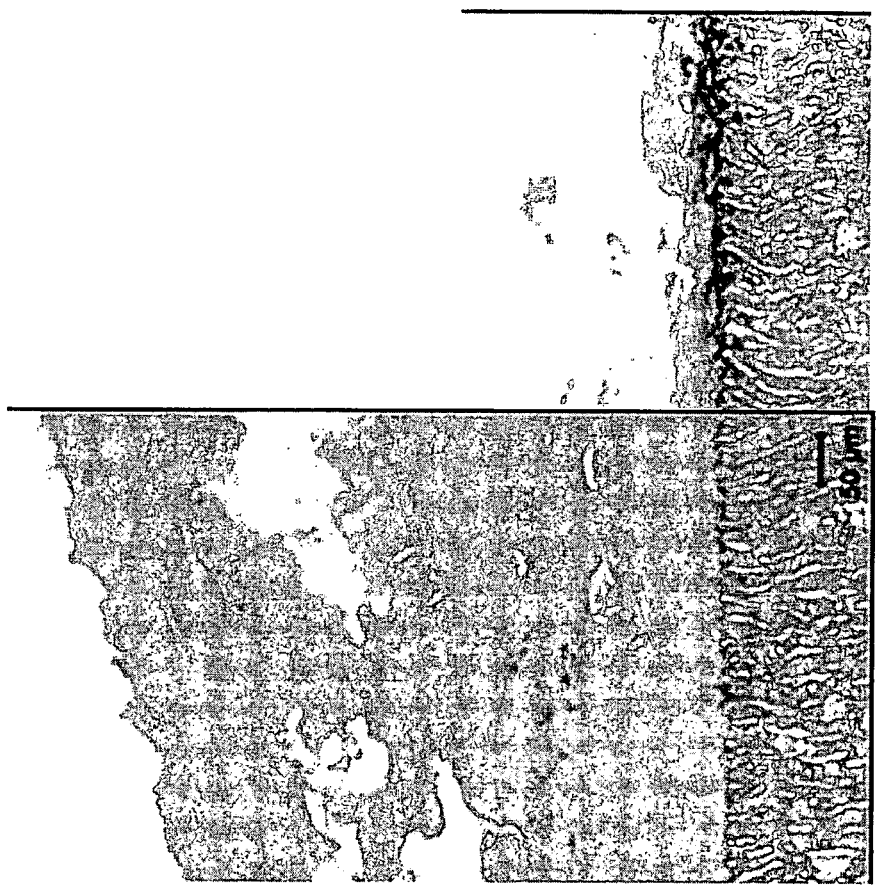
FIG. 8 shows on the right an ePTFE vascular graft sodded for 1 hour with porcine microvascular endothelial cells at about 50 mmHg pressure, implanted in a porcine ex vivo model, and subjected to supraphysiologic blood flow rates. Shown on the left is a dry ePTFE graft implanted in the same ex vivo model.

EXAMPLE 4 ePTFE grafts were prepped by being cleared with 70% ethanol, then 100% ethanol, each for 10 minutes, then transferred into culture media (M199 with 20% FBS) and stored overnight. Cells were porcine microvascular endothelial cells, isolated with collagenase digestion immediately before being pressure sodded onto the graft. Cells were pressure sodded with ~50 mmHg pressure for 1 hour before implantation. Implantation was in a porcine ex vivo model, including a femoral AV shunt for 40 minutes. Flow varied from 140-90 ml/min, supraphysiologic flow for coronary arteries (40 ml/min). Samples were then paraffin embedded and stained for hematoxylin and eosin. As a control graft without cell sodding we used commercially available ePTFE and subjected it to the same AV shunt model. FIG. 8 shows the control and ePTFE vascular graft sodded for 1 hour with porcine microvascular endothelial cells at about 50 mmHg pressure, implanted in a porcine ex vivo model, and subjected to supraphysiologic blood flow rates.

EXAMPLE 5

Figure 9:
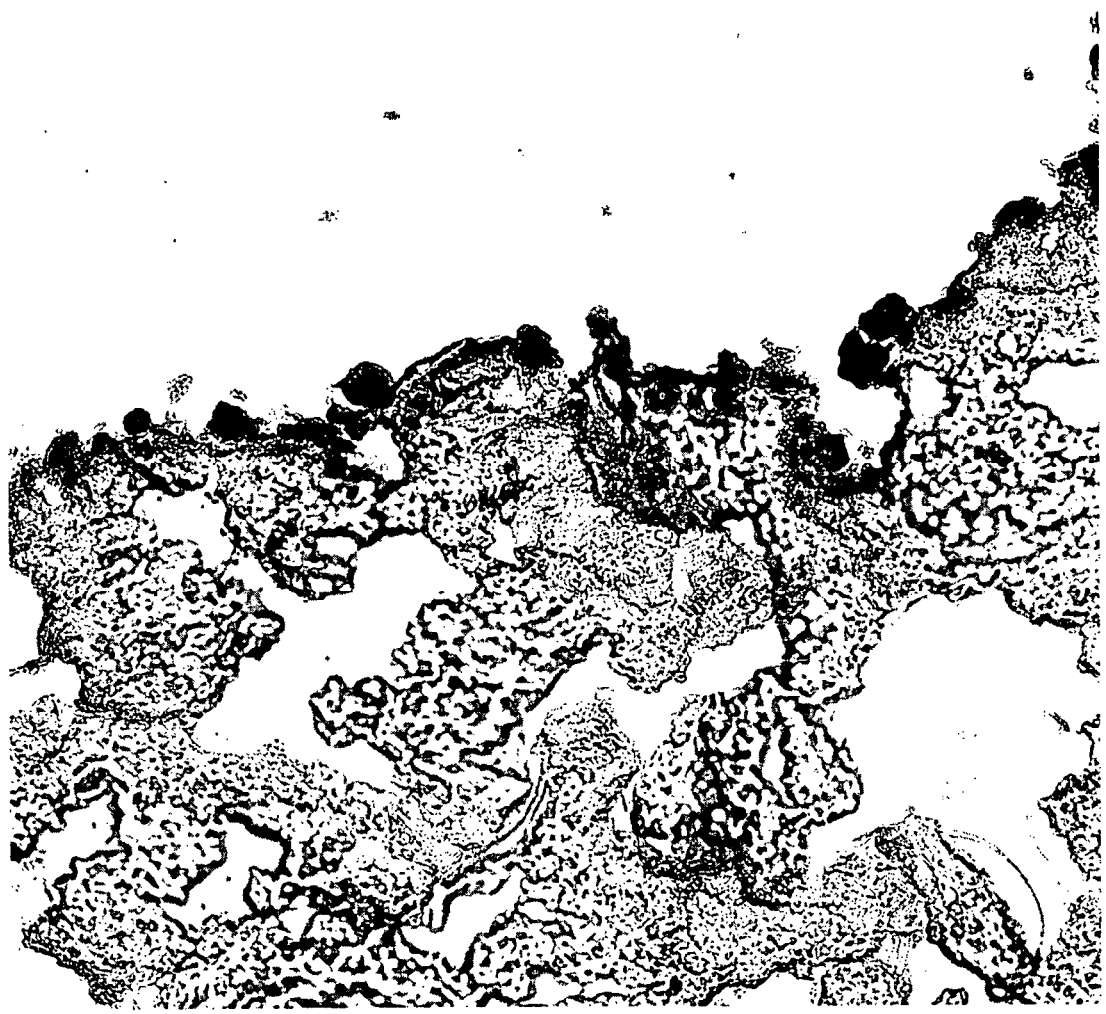
FIG. 9 shows a 40× image of an ePTFE graft sodded in a biochamber in accordance with the present invention in a BOS automated perfusion system for 5 minutes with human umbilical vein endothelial cells at 50 mmHg transmural pressure, and stained for von Willebrand Factor.

We sodded human umbilical vein endothelial cells onto an ePTFE graft for 5 minutes with 50 mmHg transmural pressure. From the sodded ePTFE, a 3 mm cross section was cut and fixed in 10% formalin. This portion of the graft material was then embedded in paraffin and sectioned at 6 um. Sections were air dried overnight and heated for 15 minutes in a 59 degree C. oven before staining with vWF (DAKO-EPOS anti-vWF/HRP (1:1 TBS) (brown)). We counter-stained with copper sulfate 0.5% and 1% Methyl green (in 0.1 N acetate buffer). FIG. 9 shows a 40× image of an ePTFE graft sodded for 5 minutes with human umbilical vein endothelial cells at 50 mmHg transmural pressure, and stained for von Willebrand Factor.

We have demonstrated that a sustained pressure head, applied to a liquid medium with suspended cells across a permeable scaffold material, offers the advantage of rapid cell adhesion, without large pressure gradients as used in transient pressure sodding techniques. One skilled in the art could readily practice the invention with a myriad of cell types, scaffold materials and geometries with any number of pumps designs. Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

What is claimed as new and desired to be protected by Letters Patent of the United States is:

1. A method of preparing a tissue graft for implantation into a patient, comprising:
   providing a porous substrate having a first side and a second side; and
   applying a transmural flow of a suspension of cells across the wall of the substrate from the first side to the second side, wherein there is a defined transmural pressure gradient of about 10 to about 60 mmHg between the first side and the second side, and wherein the transmural flow and the defined pressure are sustained for a duration sufficient to adhere the cells to the substrate, said duration being at least 5 minutes.

2. The method of claim 1, wherein the substrate has a tubular configuration for a vascular tissue graft, and wherein one of the first or second sides is the inner side of the tubular substrate, and the other of the first or second sides is the outer side of the tubular substrate.

3. The method of claim 1, wherein the pressure gradient is from about 10 mmHg to about 55 mmHg.

4. The method of claim 1, wherein the pressure gradient is from about 35 mmHg to about 50 mmHg.

5. The method of claim 1, wherein the pressure gradient is about 50 mmHg.

6. The method of claim 1, wherein the duration is about 7 minutes to about 1 hour.

7. The method of claim 1, wherein the cells are endothelial cells.

8. The method of claim 1, wherein the cells are microvascular endothelial cells.

9. The method of claim 8, wherein the microvascular endothelial cells are derived from adipose tissue.

10. The method of claim 9, further comprising harvesting the adipose tissue from said patient.

11. The method of claim 9, wherein the cells comprise a mixture of microvascular endothelial cells and adult stem cells.

12. The method of claim 11, wherein the cells are autologous.

13. The method of claim 1, wherein the substrate comprises a material selected from the group consisting of elastin, ePTFE, collagen, polyurethane, polypropylene, polyethylene, polyamides, nylon, polyethylene terephthalate, polycarbonate, and silicone.

14. The method of claim 2, further comprising applying translumenal flow through the tubular graft after the cells have adhered to the substrate and before implantation of the graft into the patient.

15. The method of claim 14, wherein the translumenal flow is at a physiological flow rate.

16. The method of claim 1, wherein the graft is pretreated with a material selected from the group consisting of protein and plasma.

17. The method of claim 16, wherein the graft is pretreated with albumin.

18. The method of claim 1, wherein the graft is rotated longitudinally at least once during transmural flow.

* * * * *